United States Patent [19]
Müller et al.

[11] Patent Number: 5,037,926
[45] Date of Patent: Aug. 6, 1991

[54] UREA-CONTAINING (METH)ACRYLIC ACID DERIVATIVES OF TRIISOCYANATES

[75] Inventors: Michael Müller, Bergisch-Gladbach; Wolfgang Podszun; Jens Winkel, both of Cologne, all of Fed. Rep. of Germany

[73] Assignee: Bayer Aktiengesellschaft, Leverkusen, Fed. Rep. of Germany

[21] Appl. No.: 620,228

[22] Filed: Nov. 20, 1990

Related U.S. Application Data

[62] Division of Ser. No. 517,261, May 1, 1990.

[30] Foreign Application Priority Data

May 27, 1989 [DE] Fed. Rep. of Germany ....... 3917320

[51] Int. Cl.⁵ .......................................... C08F 226/02
[52] U.S. Cl. ..................................... 526/301; 526/302
[58] Field of Search ................................ 526/301, 302

[56] References Cited

U.S. PATENT DOCUMENTS

| | | | |
|---|---|---|---|
| 4,744,827 | 5/1988 | Winkel et al. | 106/35 |
| 4,744,828 | 5/1988 | Winkel et al. | 106/35 |
| 4,752,338 | 6/1988 | Reiners et al. | 106/35 |
| 4,868,325 | 9/1989 | Reiners et al. | 560/115 |

FOREIGN PATENT DOCUMENTS

| | | |
|---|---|---|
| 0209365 | 1/1987 | European Pat. Off. . |
| 0266589 | 5/1988 | European Pat. Off. . |
| 2308036 | 10/1973 | Fed. Rep. of Germany . |

Primary Examiner—Joseph L. Schofer
Assistant Examiner—M. Nagumo
Attorney, Agent, or Firm—Sprung Horn Kramer & Woods

[57] ABSTRACT

For filling and forming teeth, novel (meth)acrylic acid derivatives of triisocyanates of the formula

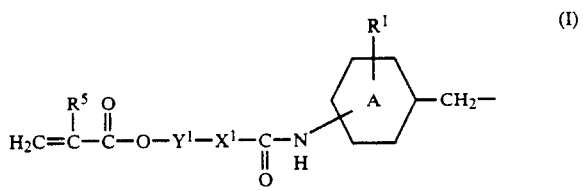

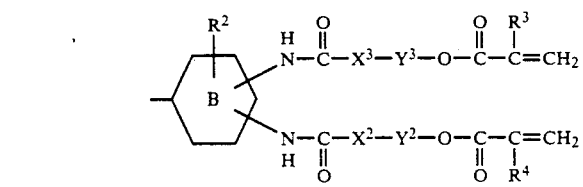

wherein
$R^1$ and $R^2$ are identical or different and stand for hydrogen or a lower alkyl radical,
$R^3$, $R^4$ and $R^5$ are identical or different and denote hydrogen or methyl,
$Y^1$ to $Y^3$ are identical or different and denote divalent straight-chain or branched hydrocarbon radicals of 2 to 15 carbon atoms which may optionally include 1 to 3 oxygen bridges and which may be unsubstituted or substituted by 1 to 4 additional (meth)acryloyloxy radicals,
$X^1$ to $X^3$ are identical or different and denote $-NR^1-$ or $-O-$, at least one of the radicals $X^1$ to $X^3$ denoting $-NR^1-$, and the rings A and B are identical or different and may be aromatic or saturated.

8 Claims, No Drawings

UREA-CONTAINING (METH)ACRYLIC ACID DERIVATIVES OF TRIISOCYANATES

This is a division of application Ser. No. 517,261 filed May 1, 1990, now pending.

The invention relates to novel urea group-containing acrylic acid and methacrylic acid derivatives of triisocyanates, referred to subsequently as (meth)acrylic acid derivatives, and to the preparation thereof The novel compounds may be employed as monomers for use in dentistry.

Novel urea group-containing (meth)acrylic acid derivatives of triisocyanates of the formula

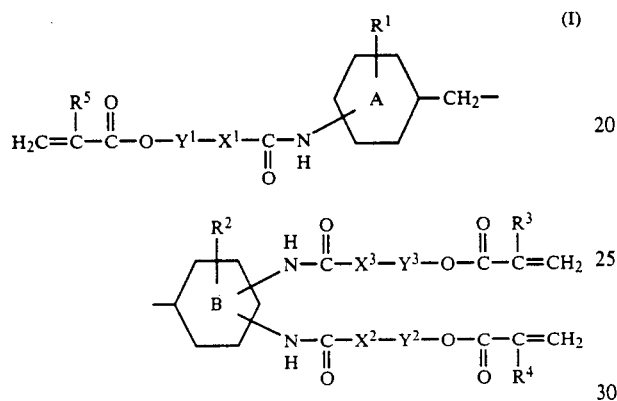

have been found; in this formula
- $R^1$ and $R^2$ are identical or different and stand for hydrogen or a lower alkyl radical,
- $R^3$, $R^4$ and $R^5$ are identical or different and denote hydrogen or methyl,
- $Y^1$ to $Y^3$ are identical or different and denote divalent straight-chain or branched hydrocarbon radicals of 2 to 15 carbon atoms which may optionally include 1 to 3 oxygen bridges and which may be unsubstituted or substituted by 1 to 4 additional (meth)acryloyloxy radicals,
- $X^1$ to $X^3$ are identical or different and denote —NR$^1$— or —O—, at least one of the radicals $X^1$ to $X^3$ denoting —NR$^1$—, $R^1$ having the meaning defined above, and the rings
- A and B are identical or different and may be aromatic or saturated.

The (meth)acrylic acid derivatives may be pure isomers or a mixture of isomers For the use according to the invention of the (meth)acrylic acid derivatives in dental materials, it is particularly advantageous to employ mixtures of isomers and derivatives, since they have a lower viscosity than compositions consisting of pure isomers.

Within the scope of the present invention, the substituents may generally have the following meanings:

Lower alkyl can denote a straight-chain or branched hydrocarbon radical of 1 to 6 carbon atoms, preferably 1 to 4 carbon atoms. The following lower alkyl radicals may be cited as examples: methyl, ethyl, propyl, isopropyl, butyl, isobutyl, pentyl, isopentyl, hexyl and isohexyl.

The divalent hydrocarbon radicals $Y^1$ to $Y^3$ can denote straight-chain or branched aliphatic hydrocarbon radicals of 2 to 15 carbon atoms, preferably 2 to 10 carbon atoms. Each of the radicals $Y^1$ to $Y^3$ may optionally include 1 to 3 oxygen bridges, preferably 1 or 2 oxygen bridges. The radicals $Y^1$ to $Y^3$ may also be substituted by 1 to 4, preferably 1 or 2 (meth)acryloyloxy radicals. The following radicals may be cited as examples:

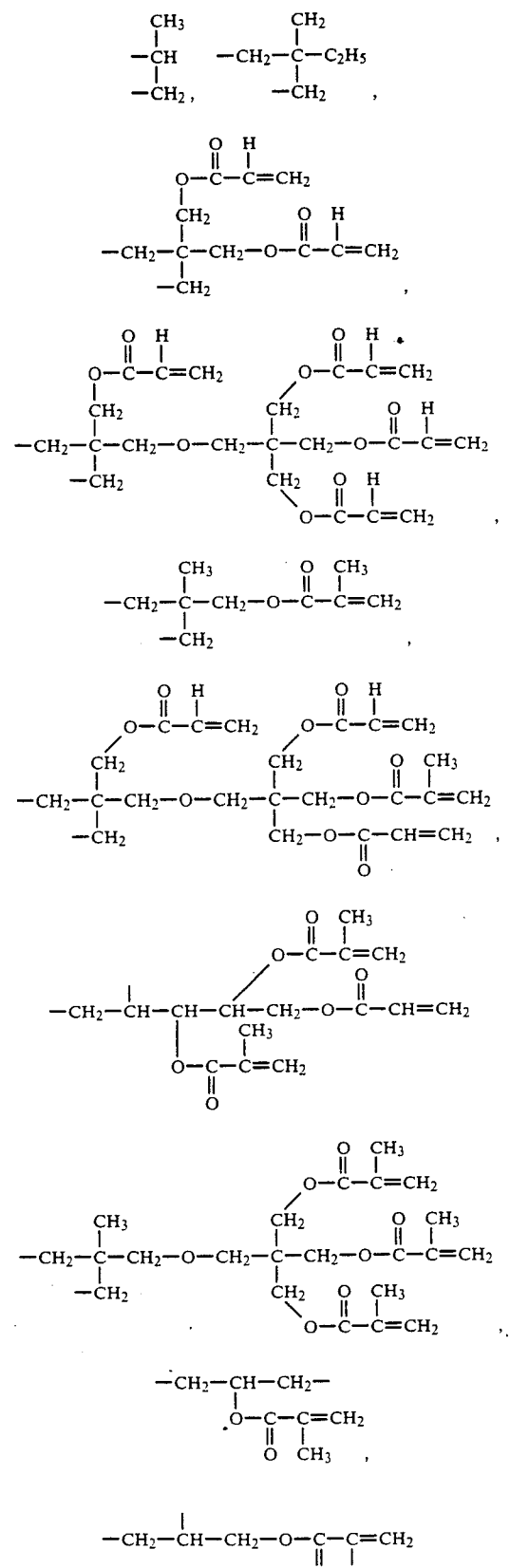

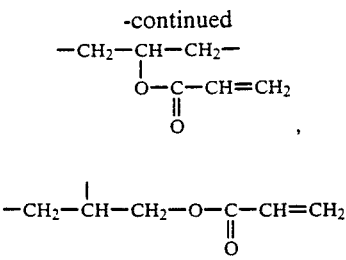

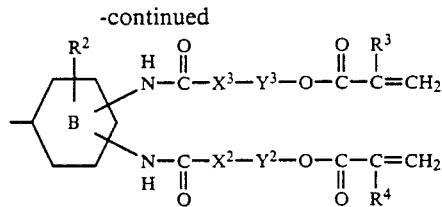

The ring A stands for a benzene nucleus or a cyclohexane radical which carries two or three substituents. The ring B stands for a benzene nucleus or a cyclohexane radical which carries three or four substituents.

The novel (meth)acrylic acid derivatives are colorless and of low volatility, and after polymerization give rise to transparent plastics of high wear resistance.

They are particularly suitable for use in dental materials, such as dental filling compounds and coatings. The materials obtained in this manner are distinguished by a surprisingly high resistance to physical and chemical stresses Compared with conventional materials used for this purpose, they are considerably harder and more fracture-resistant.

U.S. Pat. No. 4,868,325 discloses (meth)acrylic acid derivatives of triisocyanates which contain exclusively urethane groups as the bridging member between the (meth)acrylate and triisocyanate units. These compounds have essentially three crucial drawbacks which make their use more difficult. Their viscosity is so high that they have to be mixed with large amounts of comonomers which impair the properties of the cured polymers Their preparation requires prolonged reaction times, exceeding one day. In addition, their preparation takes place in a low-boiling, inert solvent which has to be exchanged for comonomers in an additional processing stage.

All three problems could be resolved with the aid of the urea groups-containing (meth)acrylic acid derivatives of triisocyanates according to the invention in that these can be prepared directly in admixture with suitable comonomers in distinctly shorter reaction times in the form of low-viscosity oils, which in view of the usually increased tendency of urea derivatives to crystallization was surprising.

Preferred compounds are (meth)acrylic acid derivatives according to the invention of the formula I

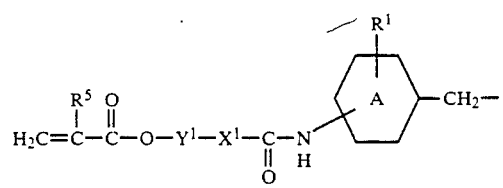
(I)

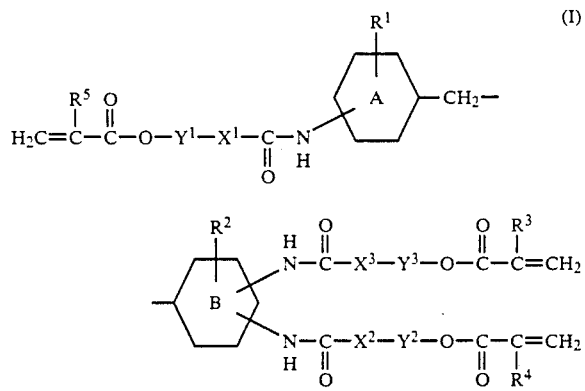

wherein
$R^1$ stands for hydrogen,
$R^2$ stands for hydrogen or an alkyl radical of 1 to 4 carbon atoms,
$R^3$, $R^4$ and $R^5$ are identical or different and denote hydrogen or methyl,
$Y^1$ to $Y^3$ are identical or different and denotes divalent straight-chain or branched aliphatic hydrocarbon radicals of 2 to 10 carbon atoms which may optionally include 1 or 2 oxygen bridges and which may be unsubstituted or substituted by 1 to 2 additional (meth)acryloyloxy radicals,
$X^1$ stands for —O—,
$X^2$ and $X^3$ denote —NR$^1$—, the ring B is aromatic or saturated and the ring A is saturated.

Particularly preferred are (meth)acrylic acid derivatives of the formula:

(I)

wherein
$R^1$ stands for hydrogen,
$R^2$ stands for hydrogen or methyl,
$R^3$, $R^4$ and $R^5$ are identical or different and denote hydrogen or methyl,
$Y^1$ to $Y^3$ are identical or different and denotes divalent straight-chain or branched aliphatic hydrocarbon radicals of 2 to 10 carbon atoms which may optionally include 1 or 2 oxygen bridges and which may be unsubstituted or substituted by 1 to 2 additional (meth)acryloyloxy radicals,
$X^1$ and $X^2$ stands for —O—,
$X^3$ denote —NR$^1$—, and the rings A and B are saturated.

The following (meth)acrylic acid derivatives are cited as examples:

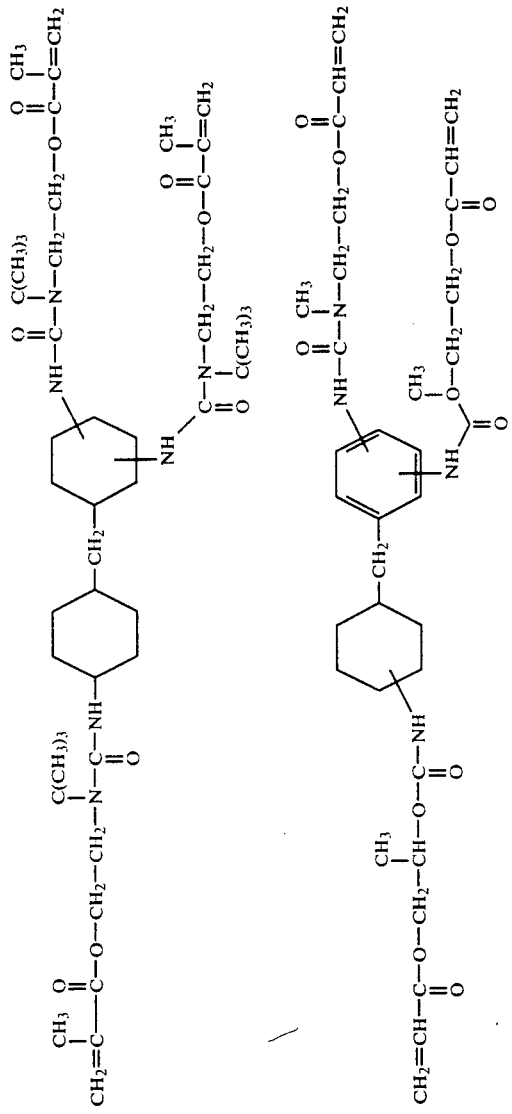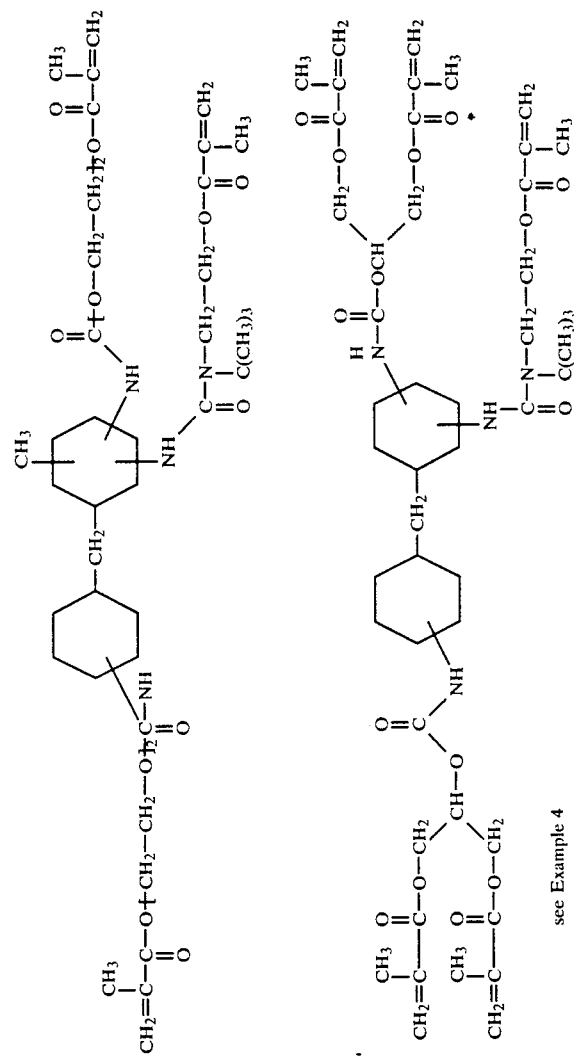
see Example 4

-continued
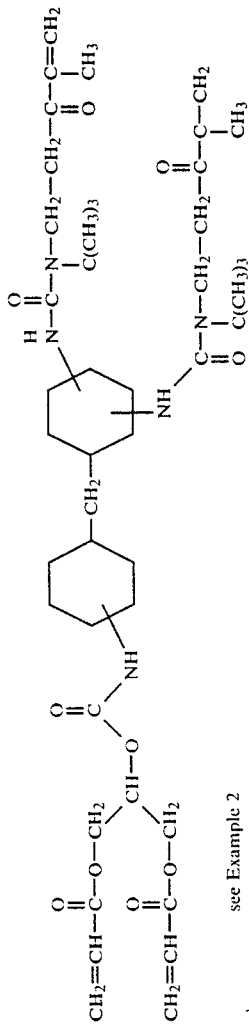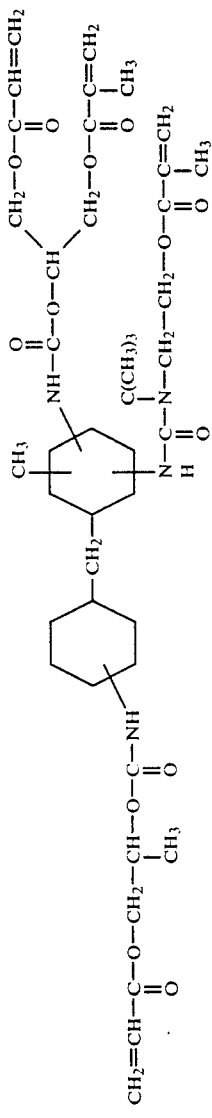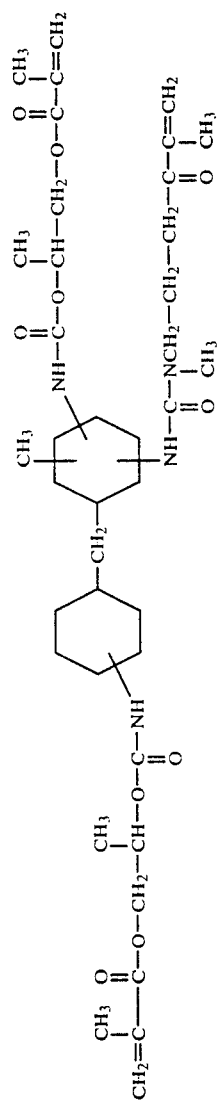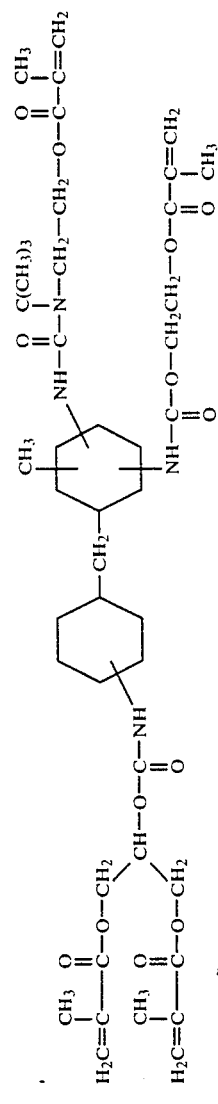
see Example 2
see Example 1

-continued
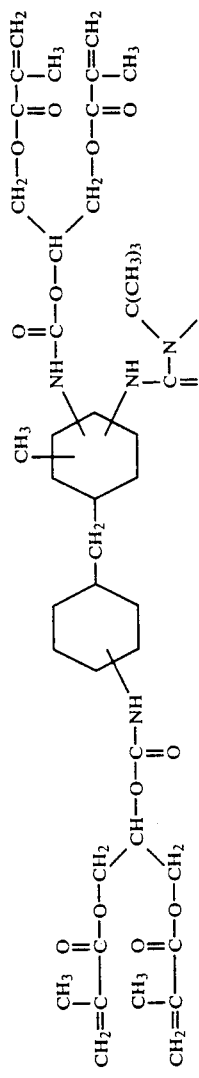
see Examples 3, 5
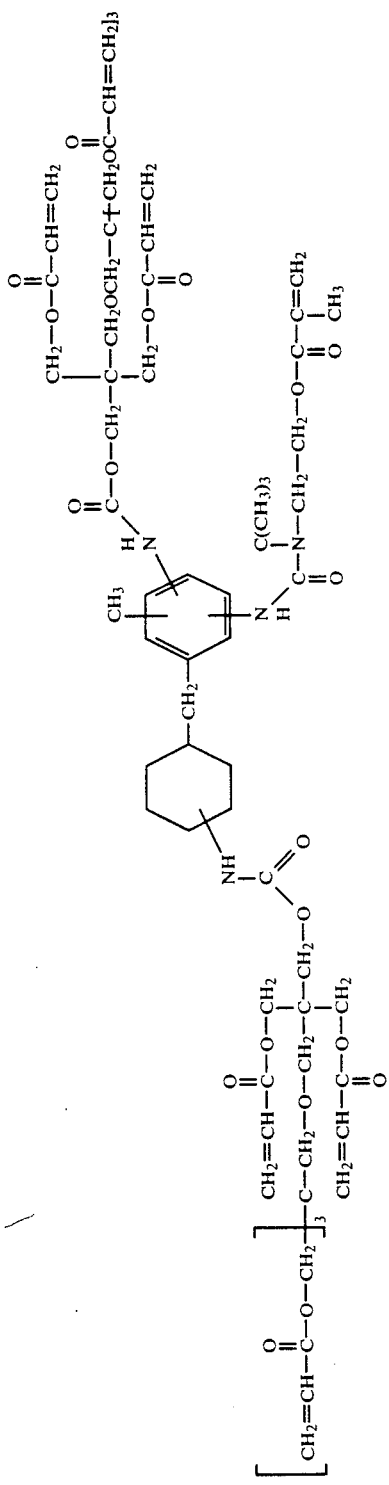

A method for the preparation of the (meth)acrylic acid derivatives according to the invention has been found which is characterized in that a triisocyanate of the formula II

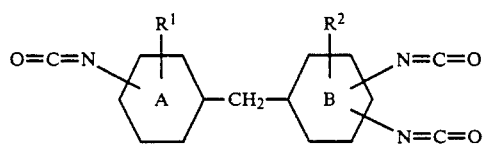

wherein
$R^1$ and $R^2$ are identical or different and stand for hydrogen or a lower alkyl radical, and the rings A and B are identical or different and may be aromatic or saturated, is reacted with aminoalkyl (meth)acrylates of the formula

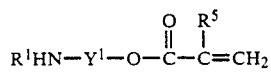

and/or

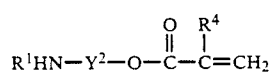

and/or

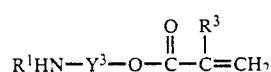

and, optionally, with hydroxyalkyl (meth)acrylates of the formula

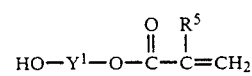

and/or

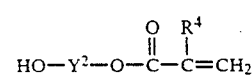

and/or

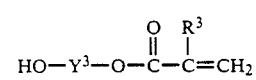

wherein
$R^1$, $R^2$ and $R^3$ are identical or different and denote hydrogen or methyl,
$Y^1$ to $Y^3$ are identical or different and denote divalent straight-chain or branched hydrocarbon radicals of 2 to 15 carbon atoms which may optionally include 1 to 3 oxygen bridges and which may be unsubstituted or substituted by 1 to 4 additional (meth)acryloyloxy radicals, and
$R^1$ has the meaning defined above.

Triisocyanates of the formula II are known (U.S. Pat. No. 4,603,189, U.S. Pat. No. 4,675,437) and may be obtained by phosgenation of the corresponding triamino compounds.

Hydroxyalkyl (meth)acrylates of the formula VI to VIII and aminoalkyl (meth)acrylates of the formula III to V are commercially available and may be prepared in a known manner by partial esterification of the corresponding polyols or by esterification of alkanolamines in the presence or absence of protective groups for the amino function.

The process according to the invention is generally carried out in such a manner that 0 to 0.8 equivalents, based on each isocyanate group of the triisocyanate (II), of a hydroxyalkyl (meth)acrylate of the formulae VI, VII or VIII and 0.2 to 1.1 equivalents of an aminoalkyl (meth)acrylate of the formulae III, IV or V or a mixture of the compounds III to VIII are employed, the total of all hydroxyl equivalents per isocyanate group having to be 0 to 0.8 and the total of al amino equivalents per isocyanate group having to be 0.2 to 1.1, in such a proportion that the total of hydroxyl and amino equivalents per isocyanate group is 0.9 to 1.1.

Preferred processes are those in which 0.3 to 0.7 equivalents, based on each isocyanate group of the triisocyanate (II), of a hydroxyalkyl (meth) acrylate of the formulae VI, VII or VIII and 0.3 to 0.7 equivalents of an aminoalkyl (meth)acrylate of the formulae III, IV or V or a mixture of the compounds III to VIII are employed, the total of all hydroxyl equivalents and the total of all amino equivalents having to be in each case 0.3 to 0.7 in such a proportion that the total of hydroxyl and amino equivalents per isocyanate group is 1.0 to 1.05.

The process according to the invention may be carried out in an inert solvent with exclusion of water. Suitable examples are chloroform, tetrahydrofuran, acetone, dioxane, methylene chloride, toluene and acetonitrile. Preferred solvents are chloroform, toluene, acetone and methylene chloride.

In particular, the process according to the invention may also take place in a reactive diluent which also contains (meth)acrylate groups, as solvent, and therefore need not be removed after the reaction, as it is copolymerizable with the compounds according to the invention. Thus, the resultant mixture of monomers is directly suitable for the preparation of dental materials. Suitable reactive diluents are monomethacrylates and dimethacrylates of dihydric alcohols such as alkanediols or ethylene glycols and propylene glycols of two to twelve carbon atoms. Hexanediol dimethacrylate and triethylene glycol dimethacrylate, ethylene glycol dimethacrylate and neopentyl glycol dimethacrylate are particularly suitable The process according to the invention is generally carried out in a temperature range from 20° to 100° C., preferably from 30° to 70° C.

The process according to the invention is generally carried out at normal pressure However, it is also possible to carry out the process in a pressure range from 1 to 15 bar.

The reaction of the isocyanate (II) according to the invention is preferably carried out with exclusion of water (preferably less than 0.1% of water).

In order to speed up the reaction, tin-containing catalysts such as dibutyltin dilaurate, stannous octoate or dibutyltin dimethoxide are preferably used.

It is also possible to use compounds comprising tertiary amino groups or titanium compounds as catalysts. The following catalysts are cited as examples: diazabicyclo[2.2.2]octane, triethylamine, N-methylpiperidine and tetrabutoxytitanium (Ullmann, Encyclopädie der technischen Chemie, vol. 19, p. 306 (1981)).

The catalyst is generally employed in an amount of 0.01 to 2.5% by weight, preferably of 0.1 to 1.5% by weight, based on the total amount of reactants.

The reaction is generally performed in the presence of 0.01 to 0.2% by weight of a polymerization inhibitor, for example 2,6-di-tert-butyl-4-methylphenol.

The process according to the invention may be carried out, for example, as follows:

The hydroxyalkyl (meth)acrylate (VI-VIII) is dissolved in a solvent and treated first with the catalyst and then with the triisocyanate (II) with stirring. When all the hydroxyl functions have reacted (IR check, NCO titration), the aminoalkyl (meth)acrylate (III-V) is added dropwise. When the isocyanate groups have reacted completely, the reaction products are isolated by removal of the solvent. A preliminary purification using adsorbents, for example activated carbon, fuller's earth, silica gel or aluminum oxide is of course also possible.

The (meth)acrylic acid derivatives of triisocyanates according to the invention may also be employed as monomers for the preparation of polymeric materials. The polymerization may be carried out in a manner known per se by a radical initiation and gives rise to polymers with a high crosslinking density.

The (meth)acrylic acid derivatives of triisocyanates according to the invention may be used particularly as monomers for dental materials. Examples of their use as dental materials are dental filling compounds, dental coatings and components for the preparation of dentures. Depending on application, dental materials may contain other auxiliary substances.

For use as monomers for dental filling compounds, or coatings (dental lacquers) in dentistry, the (meth)acrylic acid derivatives of triisocyanates according to the invention may be mixed with comonomers known per se. For example, the viscosity may be adjusted to suit the application. These mixtures of monomers generally have a viscosity in the range of 60 to 20,000 mPa.s.

The following comonomers may be cited as examples:

triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis[p-(2,-hydroxy-3'-methacryloyloxypropoxy)phenyl]propane, 2,2-bis[p-(2'-methacryloyloxyethoxy)phenyl]propane. Comonomers comprising urethan groups, for example the known reaction products of 1 mol of a diisocyanate (for example hexamethylene diisocyanate, trimethylhexamethylene diisocyanate, isophorone diisocyanate) with 2 mols of a hydroxyalkyl (meth)acrylate (for example glycerol dimethacrylate, 2-hydroxypropyl acrylate etc.) are also advantageous.

Further examples of comonomers are the following: trimethylolpropane tri(meth)acrylate, bis(meth)acryloyloxyethoxymethyl)tricyclo[5.2.1.0$^{2.6}$]decane (according to U.S. Pat. No. 4,323,696 and 4,323,348), 1,3-di-((meth)acryloyloxypropyl)-1,1,3,3-tetramethyldisiloxane, 1,3-bis(3-(meth)acryloyloxyethylcarbamoyloxypropyl)-1,1,3,3-tetramethyldisiloxane. Those comonomers which have a boiling point greater than 100° C. at 13 mbar, are particularly preferred.

Within the scope of the present invention, it is likewise preferred to use mixtures of various (meth)acrylic acid derivatives according to the invention.

The proportion of the urea group-containing (meth)acrylic acid derivatives of triisocyanates according to the invention in the mixtures of monomers is generally 10 to 90% by weight, preferably 20 to 75% by weight.

It is also possible to employ mixtures of monomers which comprise several comonomers.

The urea group-containing (meth)acrylic acid derivatives of triisocyanates according to the invention, optionally in admixture with the cited monomers, may be cured by methods known per se to yield crosslinked polymers (G. M. Brauer, H. Argentar, Am. Chem. Soc., Symp. Ser. 212, pp. 359–371 (1983)). A system consisting of a peroxidic compound and a reducing agent, for example based on tertiary aromatic amines, is suitable for the so-called redox polymerization. Examples of peroxides are: dibenzoyl peroxide, dilauroyl peroxide and di-4-chlorobenzoyl peroxide.

Examples of suitable tertiary aromatic amines are N,N-dimethyl-p-toluidine, bis(2-hydroxyethyl)-p-toluidine, bis(2-hydroxyethyl)-3,5-dimethylaniline and N-methyl-N-(2-methylcarbamoyloxypropyl)-S,5-dimethylaniline disclosed in DE-A 2,759,239.

The concentration of the peroxide and of the amine should preferably be chosen such that it is 0.1 to 5% by weight, preferably 0.5 to 3% by weight, based on the mixture of monomers. The mixtures of monomers containing peroxides and those containing amines are stored separately until used.

However, the monomers according to the invention may be also caused to polymerize by irradiation with UV light or visible light (for example in the wavelength range of 230 to 650 nm). Examples of suitable initiators for the photo-initiated polymerization are benzil, benzil dimethyl ketal, benzoin monoalkyl ether, benzophenone, p-methoxybenzophenone, fluorenone, thioxanthone, phenanthraquinone and 2,3-bornanedione (camphorquinone), in the presence or absence of synergistically acting photoactivators, such as N N-dimethylaminoethyl methacrylate, triethanolamine and 4-N,N-dimethylaminobenzenesulphonic acid bisallylamide.

The photopolymerization process is carried out, for example, as disclosed in DE-A 3,135,115.

In addition to the initiators described above, light stabilizers and polymerization inhibitors known per se for this purpose may be added.

The light stabilizer and the polymerization inhibitor are added in each case generally in an amount of 0.01 to 0.50 parts by weight, based on 100 parts by weight of the mixture of monomers. The mixtures of monomers may be used as dental coatings (dental lacquers) without the addition of fillers. A scratch-resistant coating is obtained on the substrate after the polymerization.

Fillers are generally added to mixtures of monomers for sue as dental filling compounds. Mixtures of monomers of a viscosity int he range from 60 to 20,000 mPa.s are particularly suitable for achieving a high degree of filling. Inorganic fillers may preferably be added to the mixtures of monomers comprising the compounds of the formula I. Examples of these are rock crystal, quartzite, kristobailite, quartz glass, highly disperse silicic acid, aluminum axide and glass ceramics, for example glass ceramics containing lanthanum and zirconium (U.S. Pat. No. 3,973,972).

To improve their attachment to the polymer matrix of the piolymethacrylate, the inorganic fillers are preferably pretreated with a coupling agent. The coupling may be effected, for example, by treatment with organosilicone compounds (E. P. Plueddemann, Progress in Organic Coatings, 11, 297 to 308 (1983)). 3-Methacryloyloxy-propyltrimethoxysilane is used for preference.

The fillers for use in the dental filling compounds according to the invention generally possess an average particle diameter of 0.01 to 100 μm, preferably 0.05 to 50 μm, particularly preferably 0.05 to 5 μm. It may also be advantageous to employ side by side several fillers each of which possesses a different particle diameter and a different degree of silanization.

The proportion of fillers in the dental filling compounds is generally 5 to 85% by weight, preferably 50 to 80% by weight.

To prepare the dental filling compounds, the components are processed with the aid of commercial kneaders.

The proportion of the (meth)acrylic acid derivatives according to the invention in the filling compounds is generally 5 to 90% by weight; preferably 10 to 60% by weight based on the filling compound. Curing of the dental filling compounds to a molding takes place in the cavity of the tooth, when the methods defined above are used. Because of the high wear resistance of the resultant dental filling, dental filling compounds which comprise the compounds according to the invention in polymerized form are particularly suitable for use in ancillary dentistry.

The (meth)acrylic acid derivatives of triisocyanates according to the invention may also be employed as components in the production of dentures.

For this purpose, the monomers according to the invention are combined with components known per se, used in the customary manner. The monomers are preferably used in admixture with alkyl methacrylates, such as methyl methacrylate. Bead polymers known per se may be added additionally. For the adjustment of the color of the tooth, known inorganic and organic colored pigments and opacifiers are added. The use of stabilizers and light stabilizers is likewise possible.

The artificial teeth are produced by radical polymerization of the dental compounds with appropriate shaping. Processing can take place following an injection process as well as a stamping process and is generally carried out by production methods customary for teeth based on polymethyl methacrylate, for example by heat polymerization it he presence of polymerization initiators known per se, for example those based on peroxides and azo compounds, such as dibenzoyl peroxide, dilauroyl peroxide, cyclohexyl percarbonate and azoisobutyrodinitrile. Mixtures of polyemrization initiators of different half-life periods in respect of their decomposition are likewise highly suitable.

EXAMPLES 1-4

Preparation of adducts from triisocyanates, hydroxyalkyl (meth)acrylates and aminoalkyl (meth)acryaltes The following abbreviations are used int he test below:

GDMA: glycerol dimethacrylate (an isomeric mixture of 1,3- and 1,2-bismethacryloyloxypropanol)
HDMA: hexanediol dimethacrylate (1,6-bismethacryloyloxyhexane)
HEMA: 2-hydroxyethyl methacryalte (2-methacryloyloxyethanol)
BAEMA: N-tert-butylaminoethyl methacrylate (N-tertbutyl-N-2-methacryloyloxyethylamine)
Triisocyanate: triisocyanatodicyclohexylmethane (an isomeric mixture with an NCO content of 41.5% by weight)
M-triisocyanate: triisocyanotocyclohexylmethylcyclohexylmethane (an isomeric mixture with an NCO content of 38.2% by weight)
Stabilizer: 2,6-di-tertbutyl-4-methylphenol
Catalyst: Stannous octoate General procedure for the preparation of the (meth)acrylic acid derivatives according to the invention:

To a mixture of HDMA, GDMA, stabilizer and catalyst, stirred at 30° C., feed No. 1 (triisocyanate, M-triisocyanate) is added dropwise, the reaction mixture is heated to 55-20 C. and stirred at this temperature until the GDMA is completely consumed. Feed No. 2 comprising a further hydroxyalkyl (meth)acrylate (for example HEMA) is then added and the reaction mixture is again stirred at constant temperature until this alcohol component has completely reacted as well. Feed No. 3 comprising an aminoalkyl (meth)acrylate (for example BAEMA) is then added dropwise and the reaction mixture is then stirred at 55° C. until all isocyanate groups have been completely consumed. A colorless mixture of monomers is obtained which may be used directly for the production of dental materials.

TABLE 1

| The amounts used according to the general procedure (all data are in g (mol)) | | | | |
|---|---|---|---|---|
| | Ex. 1 | Ex. 2 | Ex. 3 | Ex. 4 |
| Initial mix: | | | | |
| HDMA | 90.19 (0.355) | 96.14 (0.355) | 100.0 (0.393) | 191.39 (0.735) |
| GDMA | 54.73 (0.240) | 54.73 (0.240) | 109.45 (0.480) | 109.45 (0.480) |
| Stabilizer | 0.36 (0.002) | 0.38 (0.002) | 0.26 (0.001) | 0.37 (0.002) |
| Catalyst | 0.12 | 0.12 | 0.12 | 0.12 |
| Feed No. 1: Triisocyanate M-triisocyanate | 79.35 (0.721 NCO) | 79.35 (0.721 NCO) | 79.35 (0.721 NCO) | 72.91 (0.720 NCO) |
| Feed No. 2: HEMA | 31.25 (0.240) | — | — | — |
| Feed No. 3: BAEMA | '45.12 (0.243) | 90.24 (0.487) | 45.12 (0.243) | 45.12 (0.245) |

Example 5

The procedure of Example 3 is followed, except that the reactive diluent HDMA is replaced by 150 ml of chloroform.

At the end of the reaction the chloroform is removed in vacuo and the adduct according to the invention of M-triisocyanate, GDMA and BAEMA is obtained in the form of a colorless oil.

IR (film): γ=3360, 2920, 1720, 1640, 1519, 1450, 1320, 1298, 1158, 1007, 942, 812, 752 cm$^{-1}$.

$^1$H-NMR (CDCl$_3$, 360 MHz): δ=1.38 (s, 3H, cyclohexyl—CH$_3$), 0.9-1.6 (m, 20H, CH— and CH$_2$ of the dicyclohexylmethane unit), 1.4 (s, 9H, C(CH$_3$)$_3$), 1.93 (bs, 15H, COCCH$_3$), 3.4 (m, 2H, NCH$_2$), 4.3 (m, 10H, OCH$_2$), 5.3 (m, 2H, O—CH), 5.6, 6.12 (2m, 5H in each case, vinyl —H) ppm.

C—NMR (CDCl$_3$, 90 MHz): δ=18.3, 28.7, 29.4 (CH$_3$), approx. 30 (C of the dicyclohexylmethane unit), 43.2 (NCH$_2$), 55.9 ($\underline{C}$(CH$_3$)$_3$), 62.7 (OCH$_2$), 69.5 (O—CH), 126.2 (=CH$_2$), 135.8 (=CCH$_3$), 155.0 (O—CO—NH), 158.5 (N—CO—N), 166.7 (O—$\underline{C}$O—C) ppm.

EXAMPLE 6

0.2% by weight of camphorquinone and 0.5% by weight of 4-N,N-dimethylaminobenzenesulphonic acid bisallylamide are added to the mixture of monomers from Example 3 consisting of 70% by weight of the adduct of M-triisocyanate, GDMA and BAEMA and of 30% by weight of HDMA, and the mixture is processed int he absence of light to yield an activated mixture of monomers. This mixture is cured by visible light at a 60 sec. exposure to give rise to a plastic of high mechanical stability, which may be used as sealing material in dentistry (sealer, liner, dental lacquer).

For the preparation of a dental filling compound, 25 parts by weight of the activated mixture of monomers and 75 parts by weight of a mixture of pyrogenic silicic acid and ground quartz glasses, silanized with 3-methacryloyloxypropyltrimethoxysilane, is processed to a paste in a commercial kneader at room temperature. A test sample cured according to DIN 13,922 with the aid of a commercial dental lamp (Translux ®), produced from this paste, possesses, in addition to a high flexural modulus and a high bending strength, in particular a high abrasion resistance.

It is understood that the specification and examples are illustrative but not limitative of the present invention and that other embodiments within the spirit and scope of the invention will suggest themselves to those skilled in the art.

We claim:

1. A polymer of a (meth)acrylic acid derivative of a triisocyanate of the formula

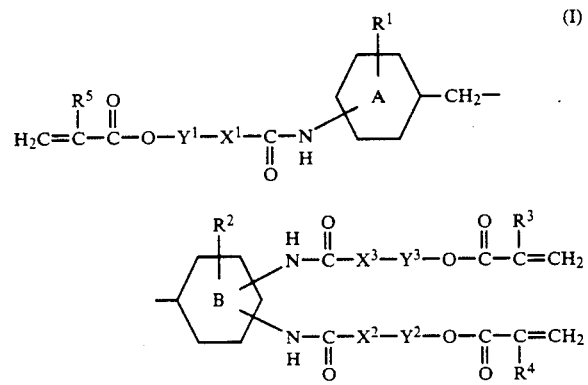

wherein
R$^1$ and R$^2$ are identical or different and stand for hydrogen or a lower alkyl radical,
R$^3$, R$^4$ and R$^5$ are identical or different and denote hydrogen or methyl, Y$^1$ to Y$^3$ are identical or different and denote divalent straight-chain or branched hydrocarbon radicals of 2 to 15 carbon atoms which may optionally include 1 to 3 oxygen bridges and which may be unsubstituted or substituted by 1 to 4 additional (meth)acryloyloxy radicals,
X$^1$ to X$^3$ are identical or different and denote —NR$^1$— or —O—, at least one of the radicals X$^1$ to X$^3$ denoting —NR$^1$—, and the rings
A and B are identical or different and may be aromatic or saturated.

2. A polymer of a (meth)acrylic acid derivative of a triisocyanate according to claim 1, wherein
R$^1$ stands for hydrogen,
R$^2$ stands for hydrogen or an alkyl radical of 1 to 4 carbon atoms,
R$^3$, R$^4$ and R$^5$ are identical or different and denote hydrogen or methyl,
Y$^1$ to Y$^3$ are identical or different and denote divalent straight-chain or branched aliphatic hydrocarbon radicals of 2 to 10 carbon atoms which may optionally include 1 or 2 oxygen bridges and which may be unsubstituted or substituted by 1 or 2 additional (meth)acryloyloxy radicals,
X$^1$ stands for —O—,
X$^2$ and X$^3$ denote —NR$^1$—,
the ring B is aromatic or saturated and the ring A is saturated.

3. A polymer of a (meth)acrylic acid derivative of a triisocyanate according to claim 1, wherein
R$^1$ stands for hydrogen,
R$^2$ stands for hydrogen or methyl,
R$^3$, R$^4$ and R$^5$ are identical or different and denote hydrogen or methyl,
Y$^1$ to Y$^3$ are identical or different and denote divalent straight-chain or branched aliphatic hydrocarbon radicals of 2 to 10 carbon atoms which may optionally include 1 or 2 oxygen bridges and which may be unsubstituted or substituted by 1 or 2 additional (meth)acryloyloxy radicals,
X$^1$ and X$^2$ stands for —O—,
X$^3$ denotes NR$^1$, and the rings
A and B are saturated.

4. A polymer of a derivative according to claim 1, formed of the following monomers in approximately the indicated molar amounts:

| HDMA | 0.355 | |
|---|---|---|
| GDMA | 0.240 | |
| M-triisocyanate | 0.721 | NCO |
| HEMA | 0.240 | |
| BAEMA | 0.243 | |

5. A polymer of a derivative according to claim 1, formed of the following monomers in approximately the indicated molar amounts;

| HDMA | 0.355 | |
|---|---|---|
| GDMA | 0.240 | |
| M-triisocyanate | 0.721 | NCO |
| BAEMA | 0.487 | |

6. A polymer of a derivative according to claim 1, formed of the following monomers in approximately the indicated molar amounts:

| | | |
|---|---|---|
| HDMA | 0.393 | |
| GDMA | 0.480 | |
| M-triisocyanate | 0.721 | NCO |
| BAEMA | 0.243 | |

7. A polymer of a derivative according to claim 1, formed of the following monomers in approximately the indicated molar amounts:

| | | |
|---|---|---|
| HDMA | 0.735 | |
| GDMA | 0.480 | |
| Triisocyanate | 0.720 | NCO |
| BAEMA | 0.245 | |

8. A polymer of a derivative according to claim 1, formed of the following monomers in approximately the indicated molar amounts:

| | |
|---|---|
| GDMA | 0.393 |
| M-triisocyanate | 0.221 |
| BAEMA | 0.243 |

* * * * *